US008202518B2

(12) United States Patent
Funaro et al.

(10) Patent No.: US 8,202,518 B2
(45) Date of Patent: Jun. 19, 2012

(54) ANTIBODIES AGAINST HUMAN CYTOMEGALOVIRUS (HCMV)

(75) Inventors: Ada Funaro, Turin (IT); Giorgio Gribaudo, Villafalletto (IT); Santo Landolfo, Turin (IT)

(73) Assignee: Ribovax Biotechnologies S.A., Petit-Lancy (CH)

( * ) Notice: Subject to any disclaimer, the term of this patent is extended or adjusted under 35 U.S.C. 154(b) by 55 days.

(21) Appl. No.: 12/667,606

(22) PCT Filed: Jun. 30, 2008

(86) PCT No.: PCT/EP2008/058360
§ 371 (c)(1),
(2), (4) Date: May 12, 2010

(87) PCT Pub. No.: WO2009/003975
PCT Pub. Date: Jan. 8, 2009

(65) Prior Publication Data
US 2010/0284916 A1    Nov. 11, 2010

(30) Foreign Application Priority Data

Jul. 4, 2007    (EP) ..................................... 07111741

(51) Int. Cl.
*A61K 39/42*   (2006.01)
*C07K 16/08*   (2006.01)
*C12Q 1/70*    (2006.01)

(52) U.S. Cl. ............. 424/147.1; 530/388.15; 530/388.3; 435/5

(58) Field of Classification Search .......................... None
See application file for complete search history.

(56) References Cited

FOREIGN PATENT DOCUMENTS

| WO | WO-9416730 A1 | 8/1994 |
|---|---|---|
| WO | WO-2007068758 A1 | 6/2007 |

OTHER PUBLICATIONS

Paul, Fundamental Immunology, (textbook), 1993, pp. 292-295, under the heading "Fv Structure and Diversity in Three Dimensions".*
Williams et al (Journal of Biological Chemistry 266:5182-5190, 1991).*
Timmerman et al (Journal of Molecular Recognition 23:559-568, 2010).*
Nejatollahi, F., et al., "Neutralising human recombinant antibodies to human cytomegalovirus glycoproteins gβ and gH." *Fems Immunology and Medical Microbiology*, vol. 34, No. 3, Nov. 15, 2002, pp. 237-244, XP002481475, The Netherlands.
Borucki, M., et al., "A phase II, double-masked, randomized, placebo-controlled evaluation of a human monoclonal anti-cytomegalovirus antibody (MSL-109) in combination with standard therapy versus standard therapy alone in the treatment of AIDS patients with cytomeglovirus." *Antiviral Research*, vol. 64, No. 2, Nov. 2004, pp. 103-111, XP004605746, The Netherlands.
Takekoshi, M., et al., "Human monoclonal anti-HCMV neutralizing antibody from phase display libraries," Journal of Virological Methods, vol. 74, No. 1, Sep. 1998, pp. 89-98, XP000996439, The Netherlands.
Foung, S., of al., "Human monoclonal antibodies to human cytomegalovirus," *The Journal of Infectious Disease*, vol. 159, No. 3, Mar. 1989, pp. 436-443, XP008096680, U.S.A.
Steenbakkers, P., et al., Efficient generation of human anti-cytomegalovirus IgG monoclonal antibodies from preselected antigent-specific B cells. *Human Antibodies and Hybridomas*, vol. 4, No. 4, Oct. 1993, pp. 166-173, XP009070174.
Urban, M., et al., "The dominant linear neutralizing antibody-binding site of gylocprotein gp86 of human cytomegalovirus is strain specific," *Journal of Virology*, vol. 66, No. 3, Mar. 1992, pp. 1303-1311, XP002497165, U.S.A.
International Search Report in PCT EP2008/058360 dated Oct. 9, 2008.

* cited by examiner

*Primary Examiner* — Mary E Mosher
(74) *Attorney, Agent, or Firm* — Marshall, Gerstein & Borun LLP (57) ABSTRACT

The present invention provides novel antibody sequences that bind human cytomegalovirus (hCMV) and neutralize hCMV infection. The novel sequences can be used for the medical management of hCMV infections, in particular for preparing pharmaceutical compositions to be used in the prophylactic or therapeutic treatment of hCMV infections.

16 Claims, 4 Drawing Sheets

gB-AD169, positions 27, 84 gB-Towne, positions 27, 84 gB(AD2)-AD169:
STSHATSSTHNGSHTSRTTSAQTRSVYSQ
HVTSSEAVSHRANETIYNTTLKYGDVVGV gB(AD2)-Towne:
STRGTSATHSHHSSHTTSAAHSRSGSVSQ
RVTSSQTVSHGVNETIYNTTLKYGDVVGV CG3 antigen

B)

gH-VR1814, positions 16, 144 gH(Ag)-VR1814:
LLSHLPSQRYGADAASEALDPHAFHLLLNTYGRPIRFLRENTTQCTYNSSLRNSTVVRENAISFN
FFQSYNQYYVFHMPRCLFAGPLAEQFLNQVDLTETLERYQQRLNTYALVSKDLASYRSFPQQLK

```
              10                          20
              |                           |
V  Q  L  Q  E  S  G  G  G  V  V  Q  P  G  R  S  L  R  L  S
gtgcagctgcaggagtcaggggggaggcgtggtccagcctgggaggtccctgagactctcc 30                          40
              |                           |
C  A  A  S  G  F  T  F  S  T  Y  G  M  H  W  V  R  Q  A  P
tgtgcagcctctggattcaccttcagtacctatggcatgcactgggtccgccaggctcca 50                          60
              |                           |
G  K  G  L  E  W  V  A  V  I  S  Y  D  G  S  S  K  Y  S  A
ggcaagggcctggagtgggtggcagttatttcatatgatggaagttctaaatactctgca 70                          80
              |                           |
D  S  V  K  G  R  F  T  I  S  R  D  N  F  K  N  T  V  Y  L
gactccgtgaagggccgattcaccatctccagagacaatttcaagaacacggtgtatttg 90                         100
              |                           |
Q  M  N  S  L  R  A  E  D  T  A  V  Y  Y  C  A  K  D  N  Y
caaatgaacagcctgagagctgaggacacagctgtgtattactgtgcgaaagacaactac 110                         120
              |                           |
S  K  Y  G  V  V  R  V  G  Y  G  M  D  V  W  G  Q  G  T  T
agtaaatacggtgtggtccgggtcggctacggtatggacgtctggggccaagggaccacg

125

V  T  V  S  S
gtcaccgtctcctca
```

B)

```
              10        20        30        40        50        60
              |         |         |         |         |         |
VH 1F7   VQLQESGGGVVQPGRSLRLSCAASGFTFSTYGMHWVRQAPGKGLEWVAVISYDGSSKYSA
              V                      ________________       _______T__
                                         HCDR1                HCDR2

70        80        90       100       110       120
              |         |         |         |         |         |
VH 1F7   DSVKGRFTISRDNFKNTVYLQMNSLRAEDTAVYYCAKDNYSKYGVVRVGYGMDVWGQGTT
                  T                              _______________________
                                                         HCDR3

125

VH 1F7   VTVSS
```

```
                   10                            20
        .  .  .  .  |  .  .  .  .  .  .  .  .  .  |
        M  T  Q  S  P  S  S  L  S  A  S  V  G  D  R  V  N  I  T  C
        atgacccagtctccatcctccctgtctgcttctgtaggagacagagtcaacatcacttgc 30                            40
        .  .  .  .  |  .  .  .  .  .  .  .  .  .  |
        R  A  S  Q  S  I  T  N  Y  L  N  W  Y  Q  Q  K  P  G  K  A
        cgggcaagtcagagcattaccaactatttaaattggtatcagcagaaaccagggaaagcc 50                            60
        .  .  .  .  |  .  .  .  .  .  .  .  .  .  |
        P  R  L  L  I  Y  A  A  S  S  L  Q  S  G  V  P  S  R  F  S
        cctaggctcctgatctatgctgcatccagtttgcaaagtggggtcccatcaaggttcagt 70                            80
        .  .  .  .  |  .  .  .  .  .  .  .  .  .  |
        G  S  G  S  G  T  D  F  T  L  T  I  S  S  L  Q  P  E  D  F
        ggcagtggatctgggacagatttcactctcaccatcagcagtctgcaacctgaagatttt 90                           100
        .  .  .  .  |  .  .  .  .  .  .  .  .  .  |
        A  T  Y  F  C  Q  Q  S  Y  S  N  R  W  T  F  G  Q  G  T  K
        gcaacttacttctgtcaacagagttacagtaaccggtggacgttcggccaaggcaccaag 105
        .  .  .  .  .
        L  E  I  K  R
        ctggaaatcaaacgg
```

B)

```
                  10        20        30        40        50        60
                  .........|.........|.........|.........|.........|.........|
        VL 1F7    MTQSPSSLSASVGDRVNITCRASQSITNYLNWYQQKPGKAPRLLIYAASSLQSGVPSRFS
                                         LCDR1                  LCDR2

70        80        90       100   105
                  .........|.........|.........|.........|....
        VL 1F7    GSGSGTDFTLTISSLQPEDFATYFCQQSYSNRWTFGQGTKLEIKR
                                          LCDR3
```

ANTIBODIES AGAINST HUMAN CYTOMEGALOVIRUS (HCMV)

CROSS-REFERENCE TO RELATED APPLICATIONS

This is the U.S. national phase of international Application No. PCT/EP2008/058360, filed Jun. 30, 2008, which claims the benefit of European patent Application No. 07111741.0, filed Jul. 4, 2007.

TECHNICAL FIELD

The invention relates to novel antibody sequences isolated from human B cells having biological activities specific for a virus that infects human cells.

BACKGROUND OF THE INVENTION

Human Cytomegalovirus (hCMV) is a widespread, highly species-specific herpesvirus, causing significant morbidity and mortality in immunosuppressed or immunologically immature individuals.

Several recent reviews have analyzed hCMV biology and clinical manifestations (Landolfo S et al., 2003; Gandhi M and Khanna R, 2004; Soderberg-Naucler C, 2006a; Halwachs-Baumann G, 2006). This viral pathogen infects the majority of the population worldwide and is acquired in childhood, following contact with a bodily fluid, since the virus enters through endothelial cells and epithelial cells of the upper alimentary or respiratory systems, or through the genitourinary system. Seropositivity to hCMV is more prevalent in underdeveloped countries or in those with lower income.

Following a primary infection, hCMV can persist in specific host cells of the myeloid lineage in a latent state, replicating and disseminating in many different cell types (haematopoietic cells, epithelial cells, endothelial cells, or fibroblasts) and escaping the host immune system. In fact, even though hCMV infections are maintained under control by the immune system, total hCMV clearance is rarely achieved.

The immunocompetent host can reduce the dissemination of the virus, in particular using humoral immunity, but hCMV has developed mechanisms that allow the viral genome to remain in selected sites in a latent state, so that any situation that weakens host immune functions can lead to hCMV reactivation.

Reactivation of the virus can be associated with different stress conditions or immaturity, leading to the activation and differentiation of the hCMV-infected cells. Clinical manifestations (such as retinitis, enterocolitis, gastritis, hepatitis) can be seen following primary infection, reinfection, or reactivation. About 10% of infants are infected by the age of 6 months following transmission from their mothers via the placenta, during delivery, or by breastfeeding.

hCMV is a virus that has a linear, 230 kb, double-stranded DNA genome. The expression of the hCMV genome is controlled by a cascade of transcriptional events that leads to the synthesis of more than 200 proteins that perform a large variety of biological activities (Britt W and Mach M, 1996). The structural proteins form the virion envelope that is extremely complex and still incompletely defined. It includes glycoproteins that are homologues to structural proteins identified in other herpesviridae (gB, gH, gL, gM, and gN) and can form disulfide-linked protein complexes within the virion: gCI (including only gB), gCII (including gM and gN) and gCIII (including gH, gL, and gO). The glycoproteins gN and gM are the most abundant and, together with gH and gB, have been shown to be essential for initial interaction between the envelope of the infectious virion and the host cell, and consequently the production of infectious hCMV. For this reason, compounds targeting gB, gH, gN, or gM may inhibit hCMV infection by blocking the entry of circulating hCMV virions into cells.

Treatment of hCMV infections is difficult because there are few options. The presently available drugs that inhibit viral replication (Ganciclovir, Cidovfivir, Foscarnet, Maribavir, and others drugs under development) produce a significant clinical improvement, but suffer from poor oral bioavailability, low potency, the emergence of hCMV resistance (due to mutations in the viral targets), and dose-limiting toxicities (De Clercq E, 2003; Baldanti F and Gerna G, 2003; Gilbert C and Boivin G, 2005).

Novel means for preventing and treating hCMV infection are needed, especially for immunocompromised individuals (e.g HIV patients) and in transplantation settings. In fact, hCMV is a clinically important opportunistic pathogen in HIV patients and in organ transplant recipients, where it contributes to graft loss independently from graft rejection, resulting in morbidity and mortality. For example, a rising number of bone marrow and solid organ-transplant recipients raises the likelihood of hCMV clinical manifestations, such as hCMV retinitis, in HIV-negative patients (Wiegland T and Young L, 2006).

Thus, it is important to provide drugs for universal preemptive, prophylactic hCMV-specific treatments, for example for the prevention of hCMV disease in transplant recipients (Hebart H and Einsele H, 2004; Kalil A et al., 2005; Snydman D, 2006), in patients developing hCMV-related neuropathologies (Griffiths P, 2004) or pregnancy (Revello M and Gerna G, 2003), to prevent the vertical transmission and life-threatening hCMV infection to fetuses and neonates. In fact hCMV is the major infectious cause of birth defects (such as hearing loss, delayed development, or mental retardation) which is due to a congenital or perinatal hCMV infection transmitted by an hCMV-infected mother (Griffiths P and Walter S, 2005).

Pharmaceutical compositions against hCMV may be useful for the treatment of other, more widespread diseases (such as cardiovascular and autoimmune diseases, or some types of cancer). In fact, hCMV is considered as a possible cofactor for such diseases and is associated to mechanisms leading to cell apoptosis, differentiation, and migration. Thus, hCMV is now considered a human pathogen of growing importance, for example, for long-term complications in tumour invasiveness and immune evasion, and for autoimmune or vascular diseases such as atherosclerosis or restenosis, wherein hCMV infection may alter cellular and immunological functions (Cinatl J et al., 2004; Soderberg-Naucler C, 2006b).

An alternative way to prevent hCMV infection is vaccination, which can provide protection in an array of high-risk patient populations. However, the correlation between vaccination and the resulting immune response is not fully understood and an optimal hCMV vaccine strategy (using specific candidate antigens or live attenuated vaccines) depends on the patient population being targeted for protection. Therefore, prophylactic vaccination strategies are still under evaluation or have already failed in clinical settings (Schleiss M, 2005).

In view of the present limitations of pharmacological strategies for hCMV infections, the increasing knowledge of the host-hCMV relationship, and in particular, of the hCMV-specific immune response, makes immune-based therapies good candidates to substitute, or complement, existing strategies for the successful treatment of hCMV-associated complications (Gandhi M and Khanna R, 2004).

A possible alternative can be passive immunotherapy, consisting in the administration to individuals of pharmaceutical compositions comprising therapeutic antibodies with a defined binding specificity for a pathogenic antigen (e.g. hCMV).

This therapeutic approach has been built on the antigen-binding features of antibodies and antibody fragments directed against human or non-human therapeutic targets (Dunman P and Nesin M, 2003; Keller M and Stiehm E, 2000). Passive immunotherapy has been introduced into clinical practice, rapidly expanding the opportunities for the treatment of a wide variety of diseases (including infectious diseases, immune-mediated diseases and cancer). This approach can be particularly effective in patients whose immune system is unable to produce antibodies in the amounts and/or with the specificity required to block and/or eliminate the targeted molecule (Chatenoud L, 2005; Laffly E and Sodoyer R, 2005).

In the field of hCMV treatment, a similar approach is performed by administering intravenously human immunoglobulin preparations that are obtained by pooling human plasma with high titers of anti-CMV antibodies, and commercialized for clinical uses (under the name of Cytotect or CytoGam). However, such a therapeutic approach represents only a partially satisfactory solution for blocking hCMV infection, in particular in immuno compromised patients where potent antivirals are often co-administered (Bonaros N et al., 2004; Kocher A et al., 2003; Kruger R et al., 2003).

Obviously, purified, recombinant, human antibodies that have high affinity for antigens on the hCMV surface would represent much better drugs for passive immunization. In fact, several of the hCMV glycoproteins elicit strong host immune responses, including the production of virus-neutralizing antibodies, even though the stoichiometry of the envelope proteins is variable and may be altered to escape host immune response. This response is felt to be a key component of host immunity and represents a goal of both antibody and vaccine development.

The hCMV envelope glycoproteins B (gB) and H (gH) are targets for human CMV-neutralizing antibodies for which more detailed information are available. Sera from seropositive individuals as well as monoclonal antibodies directed against these glycoproteins inhibit HCMV infection of cell cultures in vitro. In fact, there is a correlation between anti-gB and anti-gH titers and overall neutralizing activity of convalescent sera, and a significant drop of the sera neutralizing capacity after adsorption of gB- and gH-specific antibodies. Thus, hCMV envelope glycoproteins gB and gH contain antigenic domains that induce neutralizing antibodies. (Mach M., 2006; Antibody-mediated neutralization of infectivity. In *Cytomegaloviruses. Molecular Biology and Immunology*. Reddehase, M. (ed.) Caister Academic Press, pp. 265-283).

Human monoclonal antibodies are preferable, due to the poor results obtained with murine monoclonal antibodies. However, the development of such human antibodies for hCMV treatment has been interrupted since no virological or clinical benefits were observed in studies that evaluated the efficacy of monoclonal antibodies, for example, in hematopoietic stem cell transplantation (Boeckh M et al., 2001), or in retinitis (Gilpin A et al., 2003).

Failure of different antibodies to demonstrate clinical benefits in large trials warrants further studies aimed at the selection of antibodies, in particular fully human monoclonal antibodies that efficiently neutralize hCMV. The treatment of CMV infections would benefit from having more potent pharmaceutical compositions comprising purified human monoclonal antibodies obtained from human cells maintained in cell culture conditions or, as recombinant proteins, from the expression of human genes coding for such antibodies in mammalian cells approved for regulatory purposes.

DISCLOSURE OF THE INVENTION

The present invention provides novel antibody sequences that bind and neutralize hCMV, and that can be used for preparing compositions for detecting, treating, inhibiting, preventing, and/or ameliorating hCMV infection or an hCMV-related disease.

A population of immortalized, human B cells was divided in subcultures, and each subculture was tested for the presence of antibodies in the cell culture supernatant that bind and neutralize hCMV. Among the neutralizing subcultures, the isotype and clonality was determined for the antibodies secreted by the subculture named 1F7. These antibodies recognize a segment in the hCMV envelope glycoprotein H (gH) known to be bound by antibodies that neutralize hCMV infection. The antibody secreted by this subculture has been purified and the neutralizing ability confirmed using in vitro models for hCMV infection.

The DNA sequences that encode the variable regions of the antibody secreted by the 1F7 subculture were amplified, cloned, and sequenced. The corresponding protein sequences were analyzed to identify the Complementarity Determining Regions (CDRs) that are responsible for the hCMV-specific biological activity. These sequences can be used for producing recombinant proteins having hCMV-specific binding and neutralizing properties, in the form of full antibodies, antibody fragments, or any other format of functional protein (e.g. bioactive peptide, fusion proteins) using appropriate expression vectors, host cells, and protein purification technologies.

Compositions having therapeutic, prophylactic, and/or diagnostic utility in the management of hCMV infection and hCMV-related disorders can be prepared using these recombinant proteins, or the antibodies purified from cell cultures that have been generated using the 1F7 subculture.

Further embodiments of the present invention will be provided in the following Detailed Description.

DESCRIPTION OF THE FIGURES

FIG. 1: (A) Schematic representation of the CG3 antigen that has been assembled and used in ELISA as described in the literature (Rothe M et al., 2001). The recombinant autologous interstrain fusion antigen CG3 corresponds to a combination of the gB Antigenic Domain 2 (AD2) from hCMV strains AD169 (SwissProt Acc. No. P06473; SEQ ID NO:1) and Towne (SwissProt Acc. No. P13201; SEQ ID NO:2). The AD2 region contains a site (amino acids 70-81, underlined) that is conserved in different viral strains and that has been shown to be recognized by neutralizing antibodies (Qadri I et al., 1992; Kropff P et al., 1993). (B) Schematic representation of the gH Antigen included in the gH(Ag)-GST fusion protein used for the gH-based ELISA assay. The recombinant antigen gH(Ag)-GST corresponds to an in-frame fusion between the gH amino terminal region (amino acids 16-144; SEQ ID NO:3) from the hCMV strain VR1814 (Revello M et al., 2001) and Glutathione-S-Transferase (GST). The amino terminus of gH contains a linear antibody binding site between residues 34-43 (underlined) that is recognized by neutralizing antibodies (Urban M et al., 1992).

DETAILED DESCRIPTION OF THE INVENTION

The methods of the Invention claimed in WO 07/068758 have been developed for immortalizing isotype-specific human B cells obtained from an individual, whose blood contains antibodies having biological activities of interest (e.g. binding and/or neutralizing a viral target).

Extensive screening assays can be performed using supernatants of subcultures obtained by these methods following a single step of cloning at low cell density (e.g. 50 cells or less per well). In this manner, it is possible to characterize a large repertoire of IgG-secreting subcultures and consequently to identify a number of human monoclonal IgG having the desired binding specificity for antigens and/or the desired biological activity.

In the present case, IgG-secreting cell cultures of immortalized human B cells were obtained from the blood of a human donor in which an hCMV-neutralizing activity was initially detected. This biological activity was then used to select subcultures of immortalized B cells obtained from the original polyclonal population of human immortalized B cells. Specific subcultures not only secrete a human monoclonal antibody neutralizing hCMV infection in the cell culture medium but also grow efficiently as monoclonal cell cultures. In fact, a specific subculture was expanded in large scale cell cultures from which IgG can be purified for performing the more extensive biological assays that are needed for assessing the hCMV-related clinical utility of the antibody. In parallel, the corresponding VH and VL sequences characterizing such IgG were cloned and used for recombinant expression.

Thus, a process comprising the methods described in WO 07/068758 allows the efficient immortalization, isolation, and expansion of human B cells in cell culture conditions for generating monoclonal cell cultures expressing isotype-specific, antigen-specific human monoclonal antibodies and for producing human purified or recombinant monoclonal antibodies endowed with a biological activity. This process gives access to the repertoire of human antibodies in a fast, efficient and straightforward manner. Moreover, the cells resulting from the process can be frozen and screened later and/or in parallel for different antigens.

The present invention provides novel protein sequences that are capable of binding and neutralizing hCMV and that include specific CDRs (Complementarity Determining Regions) identified in the variable regions of the heavy and light chains of the human monoclonal antibody identified in the cell culture supernatant of the 1F7 subculture, and that can be briefly indicated as the 1F7 antibody.

The data provided in the Examples show the specificity of 1F7 antibody for a specific fragment of the glycoprotein H (gH; also known as UL75, gpUL75, p86, gp86), which is an essential glycoprotein for the hCMV fusion machinery and cell tropism (Kinzler E and Compton T, 2005; Wang D and Shenk T, 2005). Moreover, following interaction with receptors on the host cell surface, gH strongly activates specific transcription factors during the earliest stages of hCMV infection. This allows hCMV to alter signal transduction pathways, resulting in various pathologies, especially in chronic inflammatory conditions (Yurochko A et al., 1999).

A number of gH-specific murine, chimeric or humanized monoclonal antibodies have been generated using different technologies and characterized as having hCMV neutralizing capacity, thus suggesting their utility for the prophylaxis or treatment of hCMV infections (WO 94/16730; WO94/09136; WO 92/11018; Simpson J et al., 1993; Hamilton A et al., 1997; Nejatollahi F et al., 2002). In particular, a human IgG1 monoclonal antibody called MSL-109 (alternatively named in the literature as EV2-7, SDZ 89-109, Sevirumab, Protovir) was shown to be safe and well tolerated. However, no statistically significant differences in hCMV antigenemia or viremia, or survival rates, were observed due to the treatment with MSL-109 alone or in combination with other antiviral compounds (Boeckh M et al., 2001; Jabs D et al. 2002; AACTG Team, 2004). Failure of MSL-109 to demonstrate clinical benefits in large trials warrants further studies aimed at the selection of fully human monoclonal antibodies directed against gH and endowed with a potent neutralizing activity, such as the 1F7 antibody.

In one embodiment, the present invention provides proteins comprising a sequence having at least 90% identity with the sequence of the HCDR3 (CDR3 of the heavy chain variable region) of the 1F7 antibody (SEQ ID NO.: 8). The level of identity should be determined on the full length of such sequence.

Figure 3:
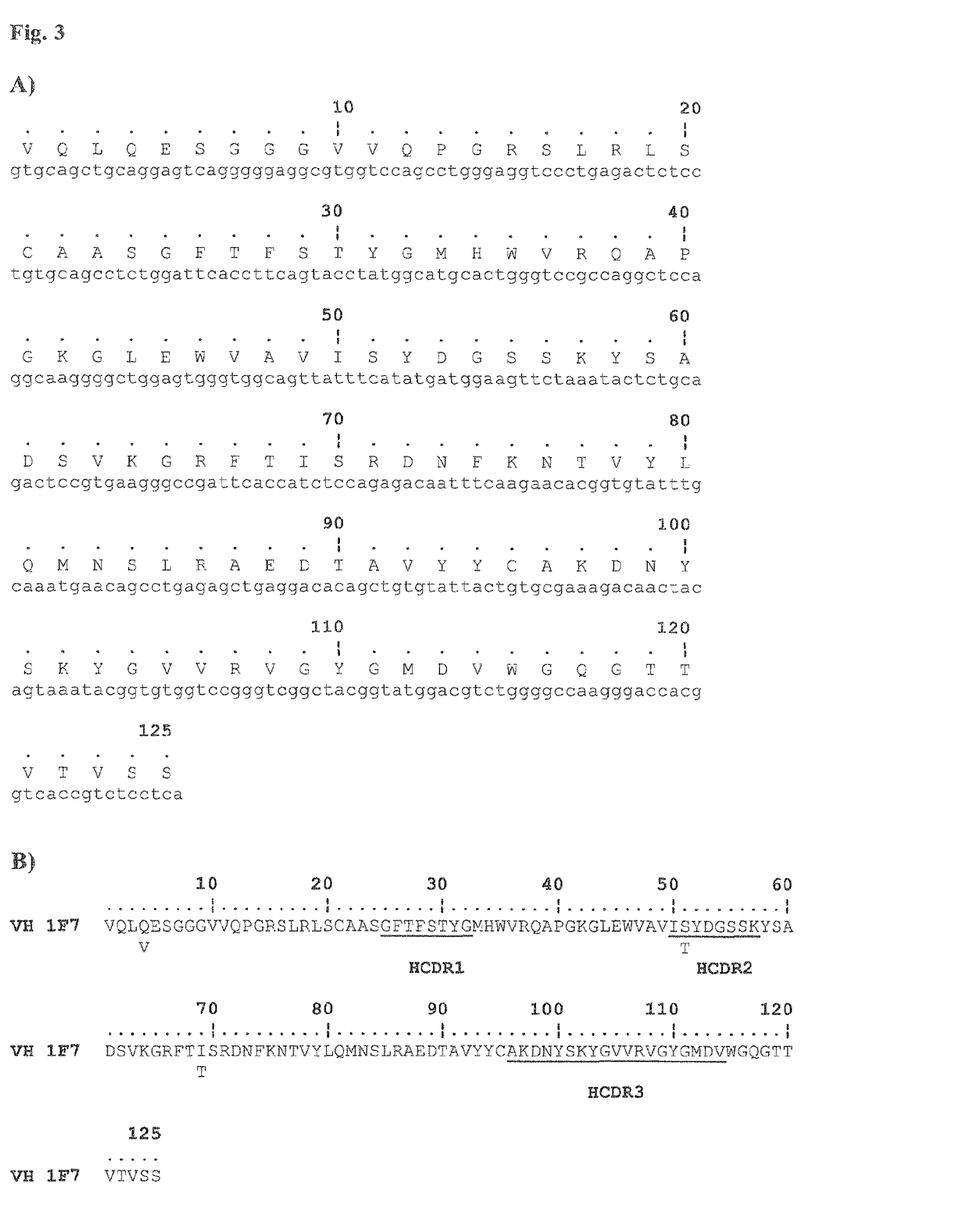
FIG. 3: (A) Alignment of the DNA (lower case) and protein (upper case) consensus sequence of the variable region for the heavy chain of the 1F7 antibody (VH 1F7; SEQ ID NO.: 4 and 5). (B) Protein consensus sequence for VH 1F7 with the indication of predicted CDRs of VH 1F7 (HCDR1, HCDR2, and HCDR3; underlined; SEQ ID NO.: 6, 7, and 8). Alternative amino acids that were encoded by the DNA sequences cloned in plasmids from isolated *E. coli* transformants are indicated below the consensus protein sequence.

Together with the HCDR1 and HCDR2 (SEQ ID NO.: 6 and SEQ ID NO.:7), this HCDR3 is included in the variable region of the heavy chain of the 1F7 antibody (VH 1F7; FIG. 3; SEQ ID NO.: 5.) This sequence is encoded by the DNA sequence (FIG. 3A; SEQ ID NO.: 4) that was amplified and cloned from cells obtained from the original subculture secreting the 1F7 antibody. Thus a protein of the invention may contain, together with the HCDR3 of the 1F7 antibody (SEQ ID NO.: 8), the sequence of the HCDR1 (SEQ ID NO.: 6) and/or HCDR2 (SEQ ID NO.: 7) of the 1F7 antibody. Such a protein may then comprise a sequence having at least 90% identity with the entire sequence of the variable region of the heavy chain of the 1F7 antibody (SEQ ID NO.: 5.)

Figure 4:
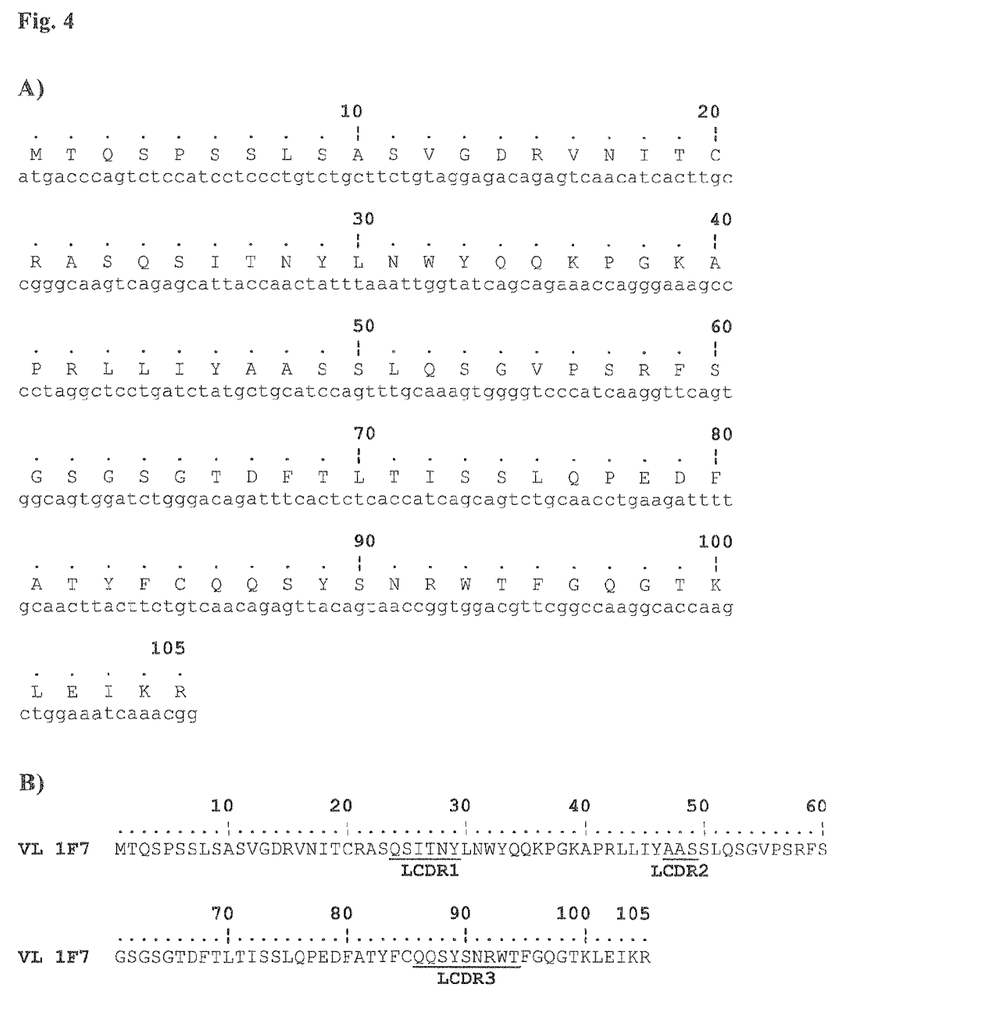
FIG. 4: (A) Alignment of the DNA (lower case) and protein (upper case) consensus sequence of the variable region for the light chain of the 1F7 antibody (VL 1F7; SEQ ID NO.: 9 and 10). (B) Protein consensus sequence for VL 1F7 with the indication of predicted CDRs of VL 1F7 (LCDR1, LCDR2, and LCDR3; underlined; SEQ ID NO.: 11, 12, and 13).

The 1F7 antibody also contains a variable region of a light chain for which, using the same approach, the DNA (SEQ ID NO.: 9) and the protein (SEQ ID NO.: 10) sequences, together with the specific LCDRs (SEQ ID NO.: 11, SEQ ID NO.: 12 and SEQ ID NO.: 13), have been determined (FIG. 4).

Thus a protein of the Invention can further comprise one or more sequences selected from the group consisting of single LCDRs of the 1F7 antibody (SEQ ID NO.: 11, SEQ ID NO.: 12 and SEQ ID NO.: 13), which can be provided as a protein sequence comprising a sequence having at least 90% identity with VL 1F7 (FIG. 4B; SEQ ID NO.: 10). This applies in particular when a human recombinant antibody, comprising both the original VL 1F7 and VH 1F7 sequence, is desired The HCDR3 of the 1F7 antibody can be considered as characterizing the antigen-binding portion of a specific human antibody that is capable of binding and neutralizing hCMV, as shown in the Examples. Even though, several or all CDRs of an antibody are generally required for obtaining an antigen-binding surface, HCDR3 is the CDR showing the highest differences between antibodies not only with respect to sequence but also with respect to length. Such diversities are fundamental components of binding regions for the recognition of essentially any antigen by the humoral immune system (Xu and Davis, 2000; Barrios Y et al. 2004; Bond C et al., 2003). Thus, hCMV-neutralizing proteins can be generated using the HCDR3 of the 1F7 antibody as an hCMV binding moiety, with or without other CDRs from the 1F7 antibody, using an antibody protein framework (Knappik A et al., 2000), or a protein framework unrelated to antibodies (Kiss C et al., 2006).

The variable regions of the heavy and light chains forming 1F7 (or selected portions, such as the isolated HCDRs and LCDRs) can be included in any other protein format for functional antibody fragments, as described in the literature under different names such as Scfv, Fab, diabody, VHH, isolated heavy or light chains, and many others (Mancini N et al., 2004; Laffly E and Sodoyer R, 2005).

Alternative antibodies can be generated using the sequences of 1F7 through a process of light-chain variable domain (VL) shuffling. In fact, several different human antibodies can be generated and tested for hCMV-specific activity using a single heavy-chain variable domain VH (such as the one of 1F7) combined with a library of VL domains, at the scope of determining VH/VL combinations with improved properties in terms of affinity, stability, and/or recombinant production (Ohlin M et al., 1996; Rojas G et al., 2004; Watkins N et al., 2004).

Moreover, novel approaches for developing new bioactive peptides also showed the feasibility of synthesizing CDR-derived peptides that contain L-amino acids and/or D-amino acids, that maintain the original activity, and that may have a good pharmacological profile (Smith J et al., 1995; Levi M et al., 2000; Wijkhuisen A et al., 2003). Thus, the HCDR3 of the 1F7 antibody, as well as sequences highly similar to HCDR3 of 1F7 antibody, fusion proteins containing it, and synthetic peptides derived from them (e.g. containing L-amino acids and/or D-amino acids, in the normal or in the retro-inverse conformation), can be tested and used as hCMV-binding and neutralizing proteins.

Moreover, it is known that antibodies may be modified in specific positions in order to have antibodies with improved features, in particular for clinical applications (such as better pharmacokinetic profile or higher affinity for an antigen). These changes can be made in the CDRs and/or framework of 1F7 and the sequence can be chosen by applying any of the dedicated technologies for the rational design of antibodies that make use, for example, of affinity maturation and other iterative processes (Kim S et al., 2006; Jain M et al., 2007).

The proteins of the invention may be provided as antibodies in general, fully human monoclonal antibodies having a specific isotype (e.g. IgG, that is the antibody format of almost all approved therapeutic antibodies) in particular, antibody fragments, bioactive peptides or fusion proteins. All these alternative molecules should maintain, if not enhance, the original hCMV binding and neutralization properties that were determined for the 1F7 antibody.

In the case of fusion proteins, the heterologous sequences can be located in the N- or C-terminal position to the 1F7-derived sequence, without affecting the correct expression and biological activity of the hCMV-specific moiety (e.g. an antibody fragment).

The term "heterologous protein" indicates that a protein sequence is not naturally present in the N- or C-terminal position to the hCMV-specific moiety (e.g. an antibody fragment). The DNA sequence encoding this protein sequence is generally fused by recombinant DNA technologies and comprises a sequence encoding at least 5 amino acids.

Such a heterologous protein sequence is generally chosen for providing additional properties to the hCMV-specific antibody fragment for specific diagnostic and/or therapeutic uses. Examples of such additional properties include: better means for detection or purification, additional binding moieties or biological ligands, or the post-translational modification of the fusion protein (e.g. phosphorylation, glycosylation, ubiquitination, SUMOylation, or endoproteolytic cleavage). Alternatively (or additionally to the fusion to a heterologous protein sequence), the activity of a protein of the invention may be improved with the conjugation to different compounds such as therapeutic, stabilizing, or diagnostic agents. Examples of these agents are detectable labels (e.g. a radio-isotope, a fluorescent compound, a toxin, a metal atom, a chemiluminescent compound, a bioluminescent compound, or an enzyme) that can be bound using chemical linkers or polymers. The hCMV-specific biological activity may be improved by the fusion with another therapeutic protein, such as a protein or a polymer altering the metabolism and/or the stability in diagnostic or therapeutic applications.

Means for choosing and designing protein moieties, ligands, and appropriate linkers, as well as methods and strategies for the construction, purification, detection and use of fusion proteins are provided in the literature (Nilsson et al., 1997; "Applications Of Chimeric Genes And Hybrid Proteins" Methods Enzymol. Vol. 326-328, Academic Press, 2000; WO01/77137) and are commonly available in clinical and research laboratories. For example, the fusion protein may contain sequences recognized by commercial antibodies (including tags such as polyhistidine, FLAG, c-Myc, or HA tags) that can facilitate the in vivo and/or in vitro identification of the fusion protein, or its purification.

Other protein sequences can be easily identified by direct fluorescence analysis (as in the case of Green Fluorescent Protein), or by specific substrates or enzymes (using proteolytic sites, for example). The stability of the hCMV-specific antibodies, antibody fragments, and fusion proteins may be improved with the fusion of well-known carrier proteins, such as phage coat protein (cp3 or cp8), Maltose Binding Protein (MBP), Bovine Serum Albumin (BSA), or Glutathione-S-Transferase (GST).

Figure 2:
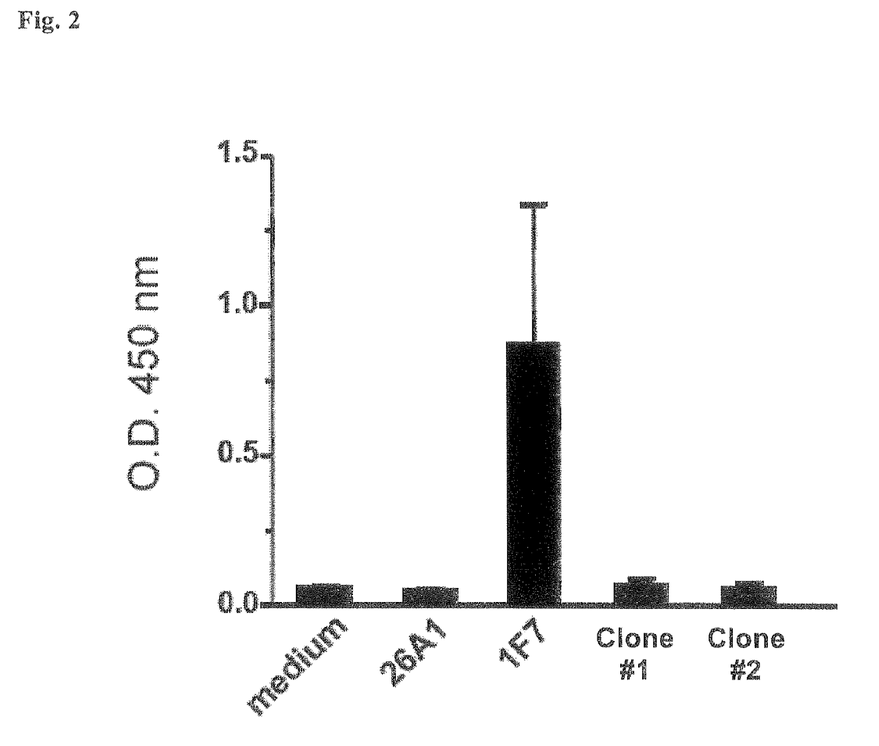
FIG. 2: gH-specific binding activity of IgG-containing supernatants from subcultures of immortalized human B cells. The ELISA was performed using the cell culture medium only (medium, negative control), or the supernatant from subcultures 26A1 (described in the patent application EP07110693), 1F7, and two other subcultures known to express hCMV-neutralizing IgG (clone #1 and #2).

The 1F7 antibody is a main object of the invention and it has been characterized, using the specific subculture supernatant, as a human IgG1 antibody which is capable of neutralizing hCMV, as determined by in vitro neutralization assays (Table 1), and to bind to a region of the hCMV gH envelope glycoprotein (FIG. 2). Consequently, this IgG antibody can be used for defining other hCMV-neutralizing proteins (e.g. in form of the antibodies, antibody fragments, bioactive peptides, fusion protein, or any natural/recombinant proteins) that are capable of neutralizing hCMV infection by binding gH in this region or in specific epitopes contained within. These properties can be tested using the assay described in the examples, or in any other hCMV specific assay. Such competing proteins may contain (or not) the HCDR3 defined above, optionally together with HCDRs and LCDRs in part or completely identical from those originally identified in the 1F7 antibody.

Further objects of the inventions are the nucleic acids encoding any of the antibodies, antibody fragments, fusion proteins, bioactive peptides, or isolated CDRs defined above.

The examples provide such sequences in particular as encoding the full variable regions of the 1F7 heavy (SEQ ID NO.: 4) and light (SEQ ID NO.: 9) chains. These DNA sequences (or selected portions, such as those encoding the specific HCDRs and LCDRs; FIGS. 3 and 4) can be transferred in vectors for expressing them in one of the alternative formats for antibodies (e.g. full, affinity-matured, CDR-grafted, or antibody fragments) or fusion proteins.

These nucleic acids can comprise a sequence having at least 90% identity with SEQ ID NO.: 4, with or without a sequence further comprising a sequence having at least 90% identity with SEQ ID NO.: 9, depending on whether sequences from only the heavy chain of 1F7 or from both the heavy and light chains are needed. When a fully human antibody is desirable, the antibody should further comprise a heavy chain constant region selected from the group consisting of human IgG1, IgG2, IgG3, IgG4, IgM, IgA and IgE constant regions. Preferably, the heavy chain constant region is an IgG1, as in the original 1F7 antibody characterized from the 1F7 subculture, or an IgG4.

The nucleic acid sequences encoding the full variable regions of the 1F7 heavy and light chains have been cloned and characterized by means of PCR reactions and vectors transforming *E coli* cells. Such sequences can be transferred (in part or totally) within other vectors, in particular within the expression cassette of a single vector or of distinct vectors where they are operably linked to the appropriate regulatory sequences (e.g. promoters, terminator of transcription).

The original 1F7 antibody, or any other protein sequences derived from such antibody, can be expressed as a recombinant protein using such vectors for transforming the appropriate host cells.

The host cells comprising the nucleic acids of the invention can be prokaryotic or eukaryotic host cells and should allow the secretion of the desired recombinant protein. Methods for producing such proteins include culturing host cells transformed with the expression vectors comprising their coding sequences under conditions suitable for protein expression and recovering the protein from the host cell culture.

The nucleic acids and host cells can be used for producing a protein of the invention by applying common recombinant DNA technologies. Briefly, the desired DNA sequences can be either extracted by digesting the initial cloning vector with restriction enzymes, or amplified using such a vector as a template for a Polymerase Chain Reaction (PCR) and the PCR primers for specifically amplifying full variable regions of the heavy and light chains or only portions of them (e.g. HCDR3). These DNA fragments can be then transferred into more appropriate vectors for expression into prokaryotic or eukaryotic host cells, as described in books and reviews on how to clone and produce recombinant proteins, including titles in the series "A Practical Approach" published by Oxford Univ. Press ("DNA Cloning 2: Expression Systems", 1995; "DNA Cloning 4: Mammalian Systems", 1996; "Protein Expression", 1999; "Protein Purification Techniques", 2001).

The vectors should include a promoter, a ribosome binding site (if needed), the start codon, and the leader/secretion sequence, that can drive accordingly the expression of a mono or bicistronic transcript having the DNA coding for the desired protein. The vectors should allow the expression of the recombinant protein in the prokaryotic or eukaryotic host cells. A cell line substantially enriched in such cells can be then isolated to provide a stable cell line.

For eukaryotic hosts (e.g. yeasts, insect or mammalian cells), different transcriptional and translational regulatory sequences may be employed, depending on the nature of the host. They may be derived from viral sources, such as adenovirus, bovine Papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for the transient (or constitutive) repression and activation and for modulating gene expression.

The sequence encoding the recombinant protein can be adapted and recloned for making modifications at the DNA level only that can be determined, for example, using software for selecting the DNA sequence in which the codon usage and the restriction sites are the most appropriate for cloning and in expression in specific vectors and the host cells (Rodi et al., 2002; Grote A et al., 2005).

During further cloning steps, protein sequences can be added in connection to the desired antibody format (Scfv, fab, antibody fragment, fully human antibody, etc.), or to the insertion, substitution, or elimination of one or more internal amino acids. These technologies can also be used for further structural and functional characterization and optimization of the therapeutic properties of proteins in general, and of antibodies in particular (Kim S et al., 2005), or for generating vectors allowing their stable in vivo delivery (Fang J et al., 2005). For example, recombinant antibodies can also be modified at the level of structure and/or activity by choosing a specific Fc region to be fused to the variable regions (Furebring C et al., 2002), by adding stabilizing peptide sequences, (WO 01/49713), by generating recombinant single chain antibody fragments (Gilliland L et al., 1996), or by adding radiochemicals or polymers to chemically modified residues (Chapman A et al., 1999).

The DNA sequence coding for the recombinant protein, once inserted into a suitable episomal or non-homologously or homologously integrating vector, can be introduced in the appropriate host cells by any suitable means (transformation, transfection, conjugation, protoplast fusion, electroporation, calcium phosphate precipitation, direct microinjection, etc.) to transform them. Factors of importance in selecting a particular vector include: the ease with which host cells that contain the vector may be recognized and selected; the number of copies of the vector which are desired; and whether the vector is able to "shuttle" the vector between host cells of different species.

The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like, and may be cleavable or repressed if needed. The selectable marker gene can either be directly linked to the DNA gene sequences to be expressed, or introduced into the same cell by co-transfection. Additional transcriptional regulatory elements may also be needed for optimal expression.

Host cells may be either prokaryotic or eukaryotic. Amongst prokaryotic host cells, the preferred ones are *B. subtilis* and *E. coli*. Amongst eukaryotic host cells, the preferred ones are yeast, insect, or mammalian cells. In particular, cells such as human, monkey, mouse, insect (using baculovirus-based expression systems) and Chinese Hamster Ovary (CHO) cells, provide post-translational modifications to protein molecules, including correct folding or certain forms of glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognize leader sequences in cloned mammalian gene products and secrete peptides bearing leader sequences (i.e., pre-peptides).

Mammalian cell lines available as hosts for expression are known in the art and include many immortalized cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Per.C6, Bowes melanoma and human hepatocellular carcinoma (for example Hep G2) cells and a number of other cell lines. In the baculovirus system, the materials for baculovirus/insect cell expression systems are commercially available in kit form (e.g. commercialized by Invitrogen).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1 or more days in an enriched media before they are switched to selective media. The purpose of the selectable marker is to confer resistance to selection, and its presence allows growth and recovery of cells that successfully express the introduced sequences. Resistant clones of stably transformed cells may proliferate using tissue culture techniques appropriate to the cell type. A cell line substantially enriched in such cells can be then isolated to provide a stable cell line.

In the case of full recombinant human immunoglobulins, an important step is the selection of the specific isotype and constant region. Vectors specifically designed for expressing antibodies with the desired isotype and subtype (for example, human IgG1 or IgG4) are widely described in the literature. Then, the full antibodies or the fusion proteins can be expressed as recombinant proteins in prokaryotic organisms (e.g. *Escherichia coli*; Sorensen and Mortensen, 2005; Venturi et al., 2002), plants (Ma et al., 2005), or eukaryotic cells, that allow a high level of expression as transient or stable transformed cells (Dinnis D and James D, 2005). This would be required in particular when the characterization of the antibodies has to be performed using more sophisticated assays, including in vivo assays, where the half-life of the antibody can be determined. The host cells can be further selected on the basis of the expression level of the recombinant protein.

In addition, when the protein is expressed, especially as an antibody, in eukayotic host cells (mammalian cell lines, in particular), different vector and expression systems have been designed for generating stable pools of transfected cell lines (Aldrich T et al., 2003; Bianchi A and McGrew J, 2003). High level, optimized, stable expression of recombinant antibodies has been achieved (Schlatter S et al., 2005), also due to optimization of cell culture conditions (Grunberg J et al., 2003; Yoon S et al., 2004) and by selecting or engineering clones with higher levels of antibody production and secretion (Bohm E et al., 2004; Butler M, 2005;).

The antibody, the antibody fragments, the fusion proteins, and any other protein defined above as being capable of binding and neutralizing hCMV can be purified using the well-established technologies that allow the isolation of either non-/recombinant proteins from cell culture or from synthetic preparations. These technologies should provide a sufficient amount of protein (from the microgram to the milligram range) to perform a more extensive characterization and validation for hCMV-related prophylactic, diagnostic, and therapeutic uses.

To this purpose, the preparations of recombinant proteins can be tested in in vitro or in vivo assays (biochemical, tissue- or cell-based assays, disease models established in rodents or primates, biophysical methods for affinity measurements, epitope mapping, etc.), in particular using one or more of those disclosed in the Examples or in the literature for studying hCMV pathogenesis and immunobiology.

The mechanism of hCMV neutralization, in connection to the viral epitopes recognized by the 1F7 antibody and the other proteins defined above, can be characterized using the cell and/or animal models available for specific structural hCMV proteins and/or strain, as shown in the literature using panels of human sera (Navarro D et al., 1997; Klein M 1999; Weber B et al., 1993; Rasmussen L et al., 1991) or of murine monoclonal antibodies (Schoppel K et al., 1996; Simpson J et al., 1993). In the past, ELISA or Western Blot using hCMV-specific truncated proteins or synthetic peptides have been also used (Greijer A et al., 1999; Ohlin M et al., 1993) and in this way antibodies directed to hCMV have been defined according to their binding to glycoprotein H (WO 94/16730; WO 94/09136; WO 92/11018).

Then, the strict species specificity of hCMV requires particularly elaborated animal models for studying the properties of antiviral compounds (such as the 1F7 antibody) and the importance of host and hCMV genotypes, for example for intrauterine hCMV infection (Barry P et al., 2006).

The antibodies, as purified preparations from human B cell supernatants or expressed as recombinant proteins, can be further validated using organ- or cell-based in vitro assays known in the literature (Eggers M et al. 1998; Lam V et al., 2006; Reinhardt B et al., 2003; Forthal D et al., 2001; Goodrum F et al., 2002). Moreover, relevant pre-clinical tests can be made in CMV-infected animals, in particular in models where human host cells can be transplanted into immunocompromised rodents (Gosselin J et al., 2005; Thomsen M et al., 2005).

The purification of the recombinant proteins of the invention can be carried out by any of the conventional methods known for this purpose, i.e. any procedure involving extraction, precipitation, chromatography, or the like.

In particular, methods for antibody purification can make use of immobilized gel matrices contained within a column (Nisnevitch M and Firer M, 2001; Huse K et al., 2002; Horenstein A et al., 2003), exploiting the strong affinity of antibodies for substrates such protein A, protein G, or synthetic substrates (Verdoliva A et al., 2002; Roque A et al., 2004), or for specific antigens or epitopes (Murray A et al., 2002; Jensen L et al., 2004). After washing, the protein is eluted from the gel by a change in pH or ionic strength. Alternatively, HPLC (High Performance Liquid Chromatography) can be used. The elution can be carried out using a water-acetonitrile-based solvent commonly employed for protein purification.

The antibody, the antibody fragments, the bioactive peptides, the fusion proteins, and any other compound defined above can be used for detecting, treating, inhibiting, preventing, and/or ameliorating hCMV infection. To this purpose, such compounds can be used for preparing diagnostic, therapeutic, or prophylactic compositions for the management of hCMV infection. In particular such compounds can be used for preparing pharmaceutical compositions, together with any pharmaceutically acceptable vehicle or carrier, or further comprising any additional therapeutic or prophylactic agent, such as vaccines, immunomodulating or antiviral compounds. In the latter case, the literature provides some examples of such compounds acting on hCMV replication (Foscarnet, Vanganciclovir, Fomivirsen, Ganciclovir) and already tested in humans (De Clercq E, 2003.)

The compositions comprising any of the proteins (e.g. antibody, antibody fragment, fusion proteins, bioactive peptides) and of the nucleic acids defined above can be used and administered to an individual with a hCMV-related diagnostic, therapeutic, or prophylactic purpose. A method for treatment, prophylaxis, or diagnosis of hCMV, or of hCMV-related disease can comprise the administration of a protein or of a nucleic acid as above defined.

These compositions can be administered as means for passive immunization which provide therapeutic compounds (in particular therapeutic antibodies or therapeutic antibodies fragments) that, by targeting hCMV virions, can inhibit the propagation of the virus in the treated patient, and potentially block the outbreak of a viral infection in the population.

Depending on the specific use, the composition should provide the compound to the human subject (in particular a pregnant woman or any other individual that is infected by hCMV or considered at risk for hCMV due to contact with an hCMV-infected individual) for a longer or shorter period of time. To this purpose, the composition can be administered, in single or multiple dosages and/or using appropriate devices, through different routes: intramuscularly, intravenously, subcutaneously, topically, mucosally, by a nebulizer or an inhaler, as eyedrops, in biodegradable matrix materials, or microbeads. In particular, the composition may allow topical or ocular administration, that represent a useful approach given the presence of hCMV in mucosae and eye. Moreover, antibodies and antibody fragments are known to be effective when applied topically to wounds (Streit M et al., 2006), cornea (Brereton H et al., 2005) or vagina (Castle P et al., 2002).

A pharmaceutical composition should provide a therapeutically or prophylactically effective amount of the compound to the subject that allows the compound to exert its activity for a sufficient period of time. The desired effect is to improve the status of the hCMV patient by controlling hCMV infection, reactivation, and/or re-infection, and by reducing at least some of the clinical manifestations of hCMV infection, such as retinitis, pancreatitis, pneumonitis, etc. (Landolfo S et al., 2003). For example, the composition should be administered at an effective amount from about 0.005 to about 50 mg/kg/body weight, depending on the route of administration and the status of the individual.

In the case of compositions having diagnostic uses, the compound should be detected using technologies commonly established in the clinical and research laboratories for detecting virus in biological samples (e.g. ELISA or other serological assays), or, when administered to a subject in vivo, at least 1, 2, 5, 10, 24, or more hours after administration.

The detection of hCMV can be performed, using the proteins of the invention, in substitution or coupled to the known means and procedures that have been established for monitoring chronic or acute hCMV infection in populations of immunocompetent and immunocompromised hosts. These techniques showed a correlation between the data generated in vitro and the clinical status (Gilbert G, 2002; Gerna G and Lilleri D, 2006).

The clinical development and use should be based on the characterization of the antibody pharmacokinetics and pharmacodynamics (Lobo E et al., 2004) and compliancy to international requirements for the production and quality control of murine, human and engineered monoclonal antibodies for therapeutic and in vivo diagnostic use in humans (Harris R et al. 2004).

The proteins of the invention can also be used for the preparation of a composition for detecting, treating, inhibiting, preventing, and/or ameliorating other, more widespread diseases (such as cardiovascular and autoimmune diseases, or some types of cancer) that can be defined as hCMV-related diseases. In these conditions, hCMV is considered as a possible cofactor since it is well-known that this virus is associated with inflammatory processes (by stimulating the expression of Fc receptors, cell adhesion molecules, chemokines and cytokines) and with alterations to the antigen-presentation pathways (by inhibiting MHC class I and II expression) leading to cell apoptosis, differentiation, and migration, for example in blood vessels and in actively proliferating cells (Cinatl J et al., 2004; Soderberg-Naucler C, 2006b).

The invention will now be described by means of the following Examples, which should not be construed as in any way limiting the present invention.

EXAMPLES

Example 1

Production of Cell Cultures Secreting Human Monoclonal Antibodies that Neutralize hCMV Materials & Methods
Production of the Culture of Immortalized Human B Cells Peripheral blood mononuclear cells (PBMCs) were obtained from an hCMV patient (CMV5) that was selected as presenting CMV-neutralizing antibodies in the serum according to an hCMV microneutralization assay based on human Embryo Lung Fibroblasts (HELF cells) and AD169 (an hCMV laboratory strain from ATCC, cod. VR-538). The serum was also tested in an ELISA specific for human IgG binding hCMV virion proteins that is commercially available (BEIA-CMV IgG Quant; Bouty, cod. 21465) and a gB (AD2) hCMV IgG ELISA, also commercially available and described in FIG. 1A (Biotest, cod. 807035, Rothe M et al., 2001). These hCMV-specific assays have been performed as outlined in WO 07/068758 or indicated by the Manufacturer.

The EBV immortalization process to which PBMCs from CMV5 were subsequently exposed has been described in WO 07/068758. At the end of the process, the immortalized cells were washed with fresh culture medium (RPMI-1640 added with 10% Fetal Calf Serum, FCS) and put in culture for 15 days at a density of $1.5 \times 10^6$ cells/ml in 24 well plates with a feeder layer (irradiated PBMC seeded at $5 \times 10^5$ cells/well). After this expansion phase, the hCMV neutralizing activity was confirmed with the test described above.

Selection of Subcultures of Immortalized Human B Cells that Secrete IgG Antibodies that Bind to Regions of the hCMV Envelope Glycoproteins gB and gH Aliquots of the expanded cell culture (each statistically containing 20 cells) were seeded in to 96-well plates on irradiated, allogeneic PBMCs as feeder cells (50,000/well) in 100 μl IMDM (added with 10% FCS and non essential amino acids, NEAA, diluted 1× from a 100× commercial stock solution; EuroClone), with the addition of CpG2006 (1 μg/ml) and IL-2 (200 U/ml). A total of 3840 cultures were generated and, after two weeks, 50 μl of the same medium (including CpG2006 and IL-2 at the concentration indicated above) were added. After a further 1-2 weeks, the supernatants of cell cultures that presented growing and aggregated cells were tested in parallel in ELISAs that detect binding of human IgG antibodies to regions of the gB or gH hCMV envelope glycoproteins (FIGS. 1A and B, respectively).

Selection of Subcultures of Immortalized Human B Cells that Secrete hCMV Neutralizing Antibodies The hCMV neutralization assay is sensitive to the presence of CpG2006. Thus, those cultures that contained IgG antibodies that bound to either the gB or gH regions (FIG. 1) were gently washed to remove CpG2006 and replaced with medium (IMDM added with 10% FCS+NEAA) without CpG2006 or IL-2. After a further 1-2 weeks of culture, the supernatants were screened using the hCMV neutralization assay based on HELF cells and hCMV strain AD169 as previously described.

Results

Human PBMCs were obtained from a CMV patient (CMV5) presenting a significant hCMV neutralization titre in serum (50% neutralization at 1:42 dilution), together with a strong reactivity in an ELISA test based on the binding to total hCMV virion proteins. The CMV5 serum was also weakly positive to the AD2 domain of glycoprotein B (gB), one of the hCMV antigens best characterized as eliciting serum neutralizing antibodies (Mach M, 2006; Antibody-mediated neutralization of infectivity. In: Cytomegaloviruses. Molecular Biology and Immunology. Reddehase M (Ed.) Caister Academic Press, pp. 265-283). The CMV5 sera was positive in these ELISA assays because an activity of 90 AU/ml was measured using the total hCMV virion proteins (a sample is considered positive for the presence of IgG anti-hCMV when the result is at least 10 AU/ml) and an activity at ¼ dilution was measured using the gB protein (a sample is considered positive for the presence of IgG anti-gB at ¼ or higher dilutions).

Cells from the CMV5 patient were used for generating an immortalized cell culture highly enriched in B cells that secrete IgG antibodies. Subcultures were then prepared from the original bulk and the supernatants selected for the presence of antibodies that bind to regions of the gB or gH envelope glycoproteins of hHCMV (FIG. 1) and neutralizing hCMV infectivity by the microneutralization assay.

Due to the low number of cells seeded in each well (20 cells/well), each subculture presenting hCMV-neutralizing activity, should likely produce monoclonal antibodies (i.e. secreted by cells clonally originated by a single, specific immortalized cell), especially given the relatively low frequency of cells in the total B cell population that would be expected to secrete hCMV-neutralizing IgG. Further experimental activities were designed to confirm this assumption.

Example 2

Characterization of the 1F7 Monoclonal Antibody

Materials and Methods
Expansion and Characterization of the Antibody Secreted by the 1F7 Subculture The cells from the original subculture 1F7 were expanded on irradiated allogenic PBMC in IMDM medium (added with 10% FCS and NEAA), confirming the hCMV neutralizing activity at least twice during this expansion step using the hCMV microneutralization assay as described in WO 07/068758 and in Example 1. Different combinations of human cells and hCMV strains were used (see Table 1)

The isotype and the amount of antibody secreted by the 1F7 subculture was determined at 24, 48, and 72 hours using a commercial quantitative human IgG ELISA kit (Immunotek; cod. 0801182; Zeptometrix Corp.) according to manufacturer's instructions. The subclass of the 1F7 antibody was determined using a commercial assay (PeliClass human IgG subclass ELISA combi-kit; cod. RDI-M1551cib, RDI Divison of Fitzgerald Industries Intl.).

The cell culture was gradually expanded by seeding the cells contained in 1 well of a 96-well plate ($\approx 1 \times 10^5$) in to one well of a 48-well plate on irradiated allogenic PBMC in IMDM added with 5% FCS. After 5-7 days, cells were expanded in to one well of a 24-well plate in the absence of feeder layer, in IMDM added with 5% FCS.

The 1F7 cell culture supernatant was tested in immunofluorescence on non-infected HUVEC cells. Briefly, HUVEC cells ($7 \times 10^4$/ml) were seeded on gelatine-coated glass-coverslips in 24-well plates in MEM added with 10% FCS and then grown to semi-confluency. Cells were then washed twice with warm PBS and then fixed with a pre-cooled (at −20° C.) mixture of 50% acetone/50% methanol for 1 minute at room temperature (RT) and washed again with PBS. Fixed cells were permeabilized with 0.2% Triton X-100 in PBS for 20 minutes on ice, washed with PBS and incubated for 15 minutes at RT with a blocking solution (PBS added with 2% FCS). Alternatively, fixed cells were not permeabilized to determine the capability of antibodies to recognize cell surface components. In this case, fixed cells were washed with PBS and incubated for 15 minutes at RT with a blocking solution (PBS added with 2% FCS). Then, cells were incubated with 1F7 cell culture supernatant (80 µl), for 2 hours at 37° C. Cells were then washed with warm PBS (3 times) and incubated with 80 µl of FITC-conjugated rabbit anti-human IgG F(ab')2 (Jackson ImmunoResearch), to track the human IgG staining as green colour. The secondary antibodies were diluted 1:50 in PBS added with 0.05% Tween80 and left on the cells in the dark for 1 hour at 37° C. Then, cells were washed with warm PBS (3 times) and counter-stained with propidium iodide (Sigma) at a concentration of 0.25 µg/ml in PBS. The coverslips were mounted on microscope slides using one drop of Mounting Medium (Vector Laboratories). Images were recorded with an Olympus Fluoview-IX70 inverted confocal laser scanning microscope.

Figure 1:
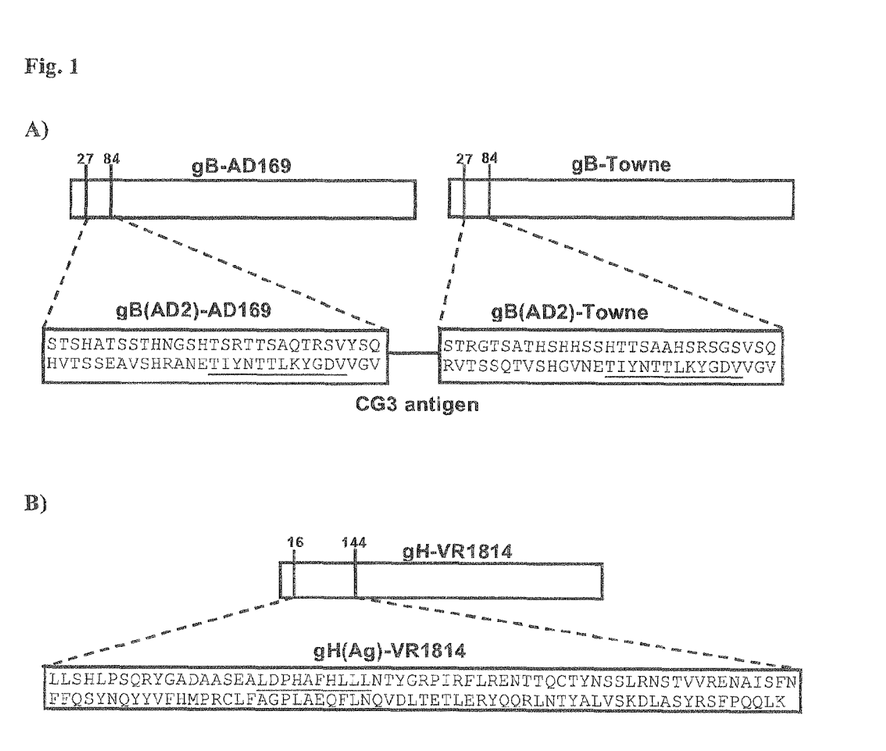

The gB AD2 and gH ELISA assays were described in Example 1 and WO 07/068758. The protein sequences of the specific hCMV antigens are shown in FIG. 1. The gH-positive supernatants were additionally tested in an ELISA assay for binding to the GST antigen used as the fusion protein in the gH ELISA. No GST-specific binding was observed, demonstrating that these supernatants bind to gH(Ag) and not GST.
Characterization of the 1F7 IgG DNA and Protein Sequence An aliquot of the cell culture, resulting from the expansion of the initial 1F7 cell culture, was used for sequencing of the variable regions of heavy chain (VH) and light chain (VL) of 1F7 antibody according to the technology established by Fusion Antibodies Ltd. Pellets of frozen cells (each containing approx. 50,000 cells) were used for extracting total RNA. The corresponding cDNA was produced by reverse transcription with an oligo(dT) primer. PCR reactions were set up to amplify the VH region using a mix of IgG specific primers, and the VL region with a mix of Igk/λ primers. The PCR products of two amplification reactions were cloned using an Eco RI restriction site in a sequencing vector (pCR2.1; Invitrogen) and used for transforming TOP10 *E. coli* cells.

At least ten colonies randomly selected from the two transformations were picked and analyzed by sequencing. The resulting DNA sequences were aligned and translated into protein sequence generating a consensus DNA and protein sequence for VH 1F7 (SEQ ID NO.: 4 and SEQ ID NO.: 5, respectively) and VL 1F7 (SEQ ID NO.: 9 and SEQ ID NO.: 10, respectively). The VH 1F7 and VL 1F7 protein sequences were compared and aligned with sequences present in databases in the public domain (using GenomeQuest, GeneSeq, and EBI databases). The CDRs characterizing VH 1F7 (SEQ ID NO.: 6, 7, and 8) and VL 1F7 (SEQ ID NO.: 11, 12, and 13) protein sequences were predicted by the IMGT database (Lefranc M, 2005).

Results

The subcultures that were obtained by dividing the bulk culture of immortalized B cells from CMV5 in 20 cell/well populations, were tested for the presence of IgG antibodies that bind to regions of the gB and gH envelope glycoproteins of hCMV using ELISA assays based on gB and gH recombinant antigens (FIG. 1).

Among the subcultures containing growing and IgG-secreting cells, the cell culture supernatants of a few of them contained antibodies that bind to a region of the gH envelope glycoprotein of hCMV. In particular, the 1F7 subculture showed the stronger and more reproducible binding to this fragment of gH (FIG. 2). Therefore, the 1F7 subculture was chosen for a more detailed molecular and biological characterization.

After washing to remove CpG2006, the supernatant from the 1F7 subculture was tested for hCMV neutralizing activity against different hCMV strains in two human host cell systems, in duplicate samples. The results showed that the hCMV neutralizing activity of the 1F7 supernatant is neither cell-type nor virus-strain specific (Table 1).

Moreover, in order to exclude that the neutralizing activity present in the supernatant from the 1F7 subculture is due to the binding to a surface component on the host cells, the supernatant was tested in immunofluorescence with uninfected HUVEC cells. This assay showed that the IgG antibodies in the supernatant from the 1F7 subculture do not bind to the uninfected human cells, confirming that the 1F7 antibody probably recognizes a neutralizing antigen within Amino Acids 16-144 of the gH envelope glycoprotein of hCMV. This supernatant was also tested in two neutralization assays for Herpes Simplex Virus (HSV)-1 and -2, based on HSV-1/-2 mutants expressing LacZ (Laquerre S et al., 1998; Peng T et al., 1998). The 1F7 supernatant showed no neutralizing activity in either the HSV-1 or the HSV-2 neutralization assay, confirming the hCMV-specific neutralizing properties of this antibody.

Larger cultures obtained using cells from the 1F7 subculture were generated by gradually expanding the culture and reducing some requirements for growth in cell culture (feeder layer, FCS in the cell culture medium). Using this approach, it was demonstrated that larger cell cultures generated from the original 1F7 subculture secrete an IgG1 antibody at a concentration of 8 µg/ml/$10^6$ cells. These larger cultures showed a doubling time of 4 days, even in the absence of feeder layer, and the hCMV neutralizing activity was maintained in culture for more than 2 months.

The monoclonality of the hCMV neutralizing antibody secreted in the 1F7-derived cell cultures was also confirmed by sequencing IgG-specific PCR products obtained from this cell culture. Cell pellets were prepared for RNA extraction and reverse transcription using cells originated from the 1F7 subculture. The resulting cDNA was then used for amplifying VH and VL sequences using specific primers for the variable regions of human IgG heavy and light chain, respectively. The PCR products were then cloned in plasmids that were used for transforming bacterial cells. Bacterial transformants were randomly picked and used for sequencing the cloned PCR products. All the clones showed the same DNA sequence, apart from minor differences possibly due to PCR-induced error, allowing the determination of consensus sequences and CDRs for the variable regions of the heavy chain (FIG. 3) and light chain (FIG. 4) of the 1F7 human monoclonal antibody.

The sequences encoding the VH and VL regions of the 1F7 antibody can be recloned in expression vectors for the appropriate expression of the 1F7 variable regions as an antibody fragment (Fab or ScFv) or within a fully human, recombinant antibody having a specific isotype and subclass (e.g. IgG1 or IgG4). These recombinant antibodies can be tested for confirming the specific hCMV neutralizing activity in the appropriate assays.

TABLE 1

| hCMV Strain | Human Cell Line | Inhibition of hCMV infection using 1F7 cell culture supernatant[a] |
|---|---|---|
| AD169[b] | HELF | ++ |
| VR1814[c] | HUVEC | ++ |

[a]+, ++, +++, and ++++ correspond to 20-40%, 41-60%, 61-80%, and more than 80% of inhibition of the hCMV infection, respectively
[b]hCMV laboratory strain (from ATCC, code VR-538)
[c]an endothelial cell-tropic derivative of a clinical isolate recovered from a cervical swab of an hCMV-infected pregnant woman (Revello M et al., 2001)

REFERENCES

AACTG Team (2004). Antiviral Res. 64, 103-111.
Aldrich T et al., (2003). Biotechnol Prog. 19, 1433-8.
Baldanti F and Gerna G, (2003). J Antimicrob Chemother. 52: 324-30.
Barrios Y et al., (2004). J Mol Recognit. 17: 332-8.
Barry P et al., (2006). ILAR J. 47: 49-64.
Bianchi A and McGrew J (2003). Biotechnol Bioeng. 84, 439-44.
Boeckh M et al., (2001). Biol. Blood Marrow Tranplant. 7: 343-351.
Bohm E et al., (2004). Biotechnol Bioeng. 88, 699-706.
Bonaros N et al., Transplantation. 2004, 77: 890-7.
Bond C et al., (2003). J Mol Biol. 332: 643-55.
Brereton H et al., (2005). Br J Ophthalmol. 89, 1205-9.
Britt W and Mach M, (1996). Intervirology, 39: 401-12.
Butler M (2005). Appl Microbiol Biotechnol. 68, 283-91.
Castle P et al., (2002). J Reprod Immunol. 56, 61-76.
Chapman A et al., (1999). Nat Biotechnol. 17: 780-3.
Chatenoud L, (2005). Methods Mol Med. 109: 297-328.
Cinatl J et al., (2004). FEMS Microbiol Rev. 28: 59-77.
De Clercq E, (2003). J Antimicrob Chemother. 51: 1079-83.
Dinnis D and James D, (2005). Biotechnol Bioeng. 91, 180-9.
Dunman P and Nesin M, (2003). Curr Opin Pharmacol. 3: 486-96.
Eggers M et al., (1998). J Med Virol. 56: 351-8.
Fang J et al., (2005). Nat Biotechnol. 23: 584-90.
Forthal D N et al., Transpl Infect Dis. 2001, 3 Suppl 2:31-4.
Furebring C et al., (2002). Mol Immunol. 38, 833-40.
Gandhi M and Khanna R, (2004). Lancet Infect Dis. 4: 725-38.
Gerna G and Lilleri D, (2006). Herpes. 13: 4-11.
Gilbert G, (2002). Med J Aust. 176: 229-36.
Gilbert C and Boivin G, (2005). Antimicrob Agents Chemother, 49: 873-83.
Gilliland L et al., (1996). Tissue Antigens. 47: 1-20.
Gilpin A et al., (2003). Control Clin Trials, 24: 92-8.
Goodrum F D et al., PNAS. 2002, 99:16255-60.
Gosselin J et al., J Immunol. 2005, 174:1587-93.
Greijer A et al., J Clin Microbiol. 1999, 37:179-88.
Griffiths P, (2004). Herpes. 11 Suppl 2: 95A-104A.

Griffiths P and Walter S. (2005). Curr Opin Infect Dis. 18: 241-5.
Grote A et al. (2005). Nucleic Acids Res. 33, W526-31.
Grunberg J et al., (2003). Biotechniques. 34, 968-72.
Halwachs-Baumann G, (2006). Curr Pharm Biotechnol. 7: 303-12.
Hamilton A et al., (1997). J Infect. Dis. 176: 59-68.
Harris R et al. (2004) Drug Development Research. 61, 137-154.
Hebart H and Einsele H, (2004). Hum Immunol. 65: 432-6.
Horenstein A et al., (2003). J Immunol Methods. 275, 99-112.
Huse K et al., (2002). J Biochem Biophys Methods. 51, 217-31.
Jabs D et al., (2002). AIDS 16: 877-887.
Jain M et al., (2007). Trends Biotechnol 25: 307-16.
Jensen L et al., (2004). J Immunol Methods. 284, 45-54.
Kalil A et al., (2005). Ann Intern Med. 143 870-80.
Keller M and Stiehm E, (2000). Clin Microbiol Rev. 13: 602-14.
Kim S et al., (2005). Mol Cells. 20: 17-29.
Kinzler E. R. and Compton T. (2005) J. Virol. 79: 7827-7837.
Kiss C et al., (2006). Nucleic Acids Res. 34: e132.
Klein M et al., (1999). J Virol. 73: 878-86.
Knappik A et al., (2000). J Mol Biol. 296: 57-86.
Kocher A et al., J Heart Lung Transpl. 2003, 22:250-7.
Kropff B et al., (1993). J Med Virol, 39, 187-95.
Kruger R et al., J Heart Lung Transpl. 2003, 22:754-63.
Laffly E and Sodoyer R, (2005). Hum Antibodies. 14: 33-55.
Lam V et al., (2006). Biotechnol Bioeng. 93: 1029-39.
Landolfo S et al., Pharmacol Ther. 2003, 98: 269-97.
Laquerre S et al., (1998). J Virol. 72: 6119-6130.
Lefranc M, (2005). Immunome Res, 1, 3.
Levi M et al., (2000). AIDS Res Hum Retroviruses. 16: 59-65.
Lobo E et al., (2004). J Pharm Sci. 93: 2645-68.
Ma J et al., (2005). Vaccine. 23: 1814-8.
Mancini N et al., (2004). New Microbiol. 27, 315-28.
Murray A et al., (2002). J Chromatogr Sci. 40, 343-9.
Navarro D et al., (1997). J Med Virol. 52: 451-9.
Nejatollahi F et al., (2002). FEMS Immunol. Med. Microbiol. 34: 237-244.
Nilsson J et al., (1997). Protein Expr Purif. 11: 1-16.
Nisnevitch M and Firer M (2001), J Biochem Biophys Methods. 49: 467-80.
Ohlin M et al., (1993). J Virol. 67: 703-10.
Ohlin M et al., (1996). Mol Immunol. 33: 47-56.
Peng T et al., (1998). J Virol. 72: 65-72.
Qadri I et al., (1992). J Gen Virol, 73 (Pt 11), 2913-21.
Rasmussen L et al., (1991). J Infect Dis. 164: 835-42.
Reinhardt B et al., J Virol Methods. 2003, 109: 1-9.
Revello M et al., (2001). J Infect Dis, 184: 1078-81.
Revello M and Gerna G, (2003). J Clin Virol. 29: 71-83.
Rodi D et al., (2002). J Mol Biol. 322, 1039-52.
Rojas G et al., (2004). J Immunol Methods. 293: 71-83.
Roque A et al., (2004). Biotechnol Prog, 20, 639-5.
Rothe M et al., (2001). J Med Virol, 65, 719-29.
Schlatter S et al., (2005). Biotechnol Prog, 21, 122-33.
Schleiss M, (2005). Herpes, 12: 66-75.
Schoppel K et al., (1996). Virology. 216: 133-45.
Simpson J et al., (1993). J Virol. 67: 489-96.
Smith J et al., (1995). J Biol Chem. 270: 30486-30490.
Snydman D, (2006). Rev Med Virol. 16: 289-95.
Soderberg-Naucler C, (2006a). Crit Rev Immunol. 26: 231-64.
Soderberg-Naucler C, (2006b). J Intern Med. 259: 219-46.
Sorensen H and Mortensen K, (2005). Microb Cell Fact. 4, 1.
Striet M et al., (2006). Int Wound J. 3: 171-9.
Thomsen M et al., (2005). Tissue Antigens. 66: 73-82.
Urban M et al., (1992). J Virol, 66: 1303-11.
Venturi M et al., (2002). J Mol Biol. 315:1-8.
Verdoliva A et al., (2002). J Immunol Methods. 271, 77-8.
Wang D and Shenk T, (2005). Proc Natl Acad Sci USA. 102: 18153-8.
Weber B et al., (1993). J Med Virol. 40: 28-34.
Watkins N et al., (2004). Tissue Antigens. 63: 345-54.
Wiegand T and Young L, (2006). Int Ophthalmol Clin. 46: 91-110.
Wijkhuisen A et al., (2003). Eur J Pharmacol. 468: 175-82.
Xu J and Davis M (2000). Immunity. 13: 37-45.
Yoon S et al., (2004). Biotechnol Prog. 20, 1683-8.
Yurochko A et al., (1999). J Immunol. 182: 4806-4816.

The invention claimed is:

1. An isolated protein comprising sequences as set out in SEQ ID NOs: 6, 7, 8, 11, 12 and 13.

2. The protein of claim 1, wherein said protein is an antibody, an antibody fragment, a bioactive peptide, or a fusion protein.

3. The protein of claim 2, wherein said antibody is a human recombinant antibody.

4. The protein of claim 2, wherein said antibody fragment is a variable heavy/light chain heterodimer, or a single-chain fragment variable.

5. The protein of claim 1, wherein said protein binds and neutralizes human Cytomegalovirus (hCMV).

6. An isolated nucleic acid encoding the protein of claim 1.

7. The nucleic acid of claim 6, wherein said nucleic acid comprises a sequence having at least 90% identity with SEQ ID NO.: 4.

8. The nucleic acid of claim 7, further comprising a sequence having at least 90% identity with SEQ ID NO.: 9.

9. A vector comprising the nucleic acid of claim 6.

10. An isolated prokaryotic or eukaryotic host cell comprising the nucleic acid of claim 6.

11. The host cell of claim 10 wherein said cell secretes said protein.

12. A therapeutic, prophylactic, or diagnostic composition for hCMV infection or for an hCMV-related disease, comprising the protein of claim 1, or the nucleic acid of claim 6.

13. The composition of claim 12 wherein the composition is for ocular or topical administration.

14. A method for the treatment of hCMV infection, or of an hCMV-related disease, comprising the administration of the protein of claim 1 or the nucleic acid of claim 6 in a therapeutically effective amount to an individual affected by an hCMV infection or hCMV-related disease, wherein said administration inhibits the propagation of hCMV in said individual.

15. A method for hCMV prophylaxis, or hCMV-related disease prophylaxis, comprising administering the protein of claim 1 or the nucleic acid of claim 6 to an individual in a prophylactically effective amount, wherein administering results in inhibition or prevention of hCMV infection.

16. A method of diagnosing hCMV infection, or hCMV-related disease, comprising contacting a sample from an individual with the protein of claim 1 and detecting binding of the protein with hCMV, wherein detecting binding of the protein to hCMV in the sample is indicative of hCMV infection in the individual from whom the sample was obtained.

* * * * *

SEQUENCE LISTING

```
<160> NUMBER OF SEQ ID NOS: 13

<210> SEQ ID NO 1
<211> LENGTH: 58
<212> TYPE: PRT
<213> ORGANISM: Human cytomegalovirus

<400> SEQUENCE: 1

Ser Thr Ser His Ala Thr Ser Ser Thr His Asn Gly Ser His Thr Ser
1               5                   10                  15

Arg Thr Thr Ser Ala Gln Thr Arg Ser Val Tyr Ser Gln His Val Thr
            20                  25                  30

Ser Ser Glu Ala Val Ser His Arg Ala Asn Glu Thr Ile Tyr Asn Thr
        35                  40                  45

Thr Leu Lys Tyr Gly Asp Val Val Gly Val
    50                  55

<210> SEQ ID NO 2
<211> LENGTH: 58
<212> TYPE: PRT
<213> ORGANISM: Human cytomegalovirus
```

<400> SEQUENCE: 2

Ser Thr Arg Gly Thr Ser Ala Thr His Ser His Ser Ser His Thr
1               5                   10                  15

Thr Ser Ala Ala His Ser Arg Ser Gly Ser Val Ser Gln Arg Val Thr
            20                  25                  30

Ser Ser Gln Thr Val Ser His Gly Val Asn Glu Thr Ile Tyr Asn Thr
        35                  40                  45

Thr Leu Lys Tyr Gly Asp Val Val Gly Val
    50                  55

<210> SEQ ID NO 3
<211> LENGTH: 129
<212> TYPE: PRT
<213> ORGANISM: Human cytomegalovirus

<400> SEQUENCE: 3

Leu Leu Ser His Leu Pro Ser Gln Arg Tyr Gly Ala Asp Ala Ala Ser
1               5                   10                  15

Glu Ala Leu Asp Pro His Ala Phe His Leu Leu Asn Thr Tyr Gly
            20                  25                  30

Arg Pro Ile Arg Phe Leu Arg Glu Asn Thr Thr Gln Cys Thr Tyr Asn
            35                  40                  45

Ser Ser Leu Arg Asn Ser Thr Val Val Arg Glu Asn Ala Ile Ser Phe
        50                  55                  60

Asn Phe Phe Gln Ser Tyr Asn Gln Tyr Tyr Val Phe His Met Pro Arg
65                  70                  75                  80

Cys Leu Phe Ala Gly Pro Leu Ala Glu Gln Phe Leu Asn Gln Val Asp
                85                  90                  95

Leu Thr Glu Thr Leu Glu Arg Tyr Gln Gln Arg Leu Asn Thr Tyr Ala
            100                 105                 110

Leu Val Ser Lys Asp Leu Ala Ser Tyr Arg Ser Phe Pro Gln Gln Leu
        115                 120                 125

Lys

<210> SEQ ID NO 4
<211> LENGTH: 375
<212> TYPE: DNA
<213> ORGANISM: Homo sapiens

<400> SEQUENCE: 4
gtgcagctgc aggagtcagg gggaggcgtg gtccagcctg ggaggtccct gagactctcc      60
tgtgcagcct ctggattcac cttcagtacc tatggcatgc actgggtccg ccaggctcca     120 ggcaagggc tggagtgggt ggcagttatt tcatatgatg gaagttctaa atactctgca     180
gactccgtga aggccgatt caccatctcc agagacaatt caagaacac ggtgtatttg      240 caaatgaaca gcctgagagc tgaggacaca gctgtgtatt actgtgcgaa agacaactac     300
agtaaatacg gtgtggtccg ggtcggctac ggtatggacg tctggggcca agggaccacg     360
gtcaccgtct cctca                                                     375

<210> SEQ ID NO 5
<211> LENGTH: 125
<212> TYPE: PRT
<213> ORGANISM: Homo sapiens

<400> SEQUENCE: 5

Val Gln Leu Gln Glu Ser Gly Gly Gly Val Val Gln Pro Gly Arg Ser

```
                1               5                  10                 15
Leu Arg Leu Ser Cys Ala Ala Ser Gly Phe Thr Phe Ser Thr Tyr Gly
                20                 25                 30

Met His Trp Val Arg Gln Ala Pro Gly Lys Gly Leu Glu Trp Val Ala
            35                 40                 45

Val Ile Ser Tyr Asp Gly Ser Ser Lys Tyr Ser Ala Asp Ser Val Lys
        50                 55                 60

Gly Arg Phe Thr Ile Ser Arg Asp Asn Phe Lys Asn Thr Val Tyr Leu
65                 70                 75                 80

Gln Met Asn Ser Leu Arg Ala Glu Asp Thr Ala Val Tyr Tyr Cys Ala
                85                 90                 95

Lys Asp Asn Tyr Ser Lys Tyr Gly Val Val Arg Val Gly Tyr Gly Met
                100                105                110

Asp Val Trp Gly Gln Gly Thr Thr Val Thr Val Ser Ser
                115                120                125

<210> SEQ ID NO 6
<211> LENGTH: 8
<212> TYPE: PRT
<213> ORGANISM: Homo sapiens

<400> SEQUENCE: 6

Gly Phe Thr Phe Ser Thr Tyr Gly
1               5

<210> SEQ ID NO 7
<211> LENGTH: 8
<212> TYPE: PRT
<213> ORGANISM: Homo sapiens

<400> SEQUENCE: 7

Ile Ser Tyr Asp Gly Ser Ser Lys
1               5

<210> SEQ ID NO 8
<211> LENGTH: 19
<212> TYPE: PRT
<213> ORGANISM: Homo sapiens

<400> SEQUENCE: 8

Ala Lys Asp Asn Tyr Ser Lys Tyr Gly Val Val Arg Val Gly Tyr Gly
1               5                   10                  15

Met Asp Val

<210> SEQ ID NO 9
<211> LENGTH: 337
<212> TYPE: DNA
<213> ORGANISM: Homo sapiens

<400> SEQUENCE: 9
atgacccagt ctccatcctc cctgtctgct tctgtaggag acagagtcaa catcacttgc      60
cgggcaagtc agagcattac caactattta aattggtatc agcagaaacc agggaaagcc    120
cctaggctcc tgatctatgc tgcatccagt ttgcaaagtg ggtcccatc  aaggttcagt    180 ggcagtggat ctgggacaga tttcactctc accatcagca gtctgcaacc tgaagatttt    240
gcaacttact tctgtcaaca gagttacagt aaccggtgga cgttcggcca aggcaccaag    300
ctggaaatca aacggactgt ggctgcacca tctgtct                              337

<210> SEQ ID NO 10
```

```
<211> LENGTH: 105
<212> TYPE: PRT
<213> ORGANISM: Homo sapiens

<400> SEQUENCE: 10

Met Thr Gln Ser Pro Ser Ser Leu Ser Ala Ser Val Gly Asp Arg Val
1               5                   10                  15

Asn Ile Thr Cys Arg Ala Ser Gln Ser Ile Thr Asn Tyr Leu Asn Trp
            20                  25                  30

Tyr Gln Gln Lys Pro Gly Lys Ala Pro Arg Leu Leu Ile Tyr Ala Ala
        35                  40                  45

Ser Ser Leu Gln Ser Gly Val Pro Ser Arg Phe Ser Gly Ser Gly Ser
    50                  55                  60

Gly Thr Asp Phe Thr Leu Thr Ile Ser Ser Leu Gln Pro Glu Asp Phe
65                  70                  75                  80

Ala Thr Tyr Phe Cys Gln Gln Ser Tyr Ser Asn Arg Trp Thr Phe Gly
                85                  90                  95

Gln Gly Thr Lys Leu Glu Ile Lys Arg
            100                 105

<210> SEQ ID NO 11
<211> LENGTH: 6
<212> TYPE: PRT
<213> ORGANISM: Homo sapiens

<400> SEQUENCE: 11

Gln Ser Ile Thr Asn Tyr
1               5

<210> SEQ ID NO 12
<211> LENGTH: 3
<212> TYPE: PRT
<213> ORGANISM: Homo sapiens

<400> SEQUENCE: 12

Ala Ala Ser
1

<210> SEQ ID NO 13
<211> LENGTH: 9
<212> TYPE: PRT
<213> ORGANISM: Homo sapiens

<400> SEQUENCE: 13

Gln Gln Ser Tyr Ser Asn Arg Trp Thr
1               5
```